US00PP11921P2

(12) United States Plant Patent
Trees

(10) Patent No.: US PP11,921 P2
(45) Date of Patent: Jun. 12, 2001

(54) GERANIUM PLANT NAMED 'BALGALSABE'

(75) Inventor: Scott C. Trees, Nipomo, CA (US)

(73) Assignee: Ball Floraplant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/476,003

(22) Filed: Dec. 31, 1999

(51) Int. Cl.[7] ..... A01H 5/00
(52) U.S. Cl. ..... Plt./324
(58) Field of Search ..... Plt./324, 325, 327, Plt./328, 329, 330, 332

(56) References Cited

U.S. PATENT DOCUMENTS

P.P. 11,490 * 8/2000 Trees ..... Plt./330

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Geranium plant named 'Balgalsabe', characterized by its semi-double dark red-colored flowers; floriferousness; upright and rounded to spreading growth habit; and freely basal-branching habit.

1 Drawing Sheet

BACKGROUND OF THE INVENTION

The present invention relates to a new and distinct cultivar of Geranium plant, botanically known as *Pelargonium×hortorum×P. peltatum,* and hereinafter referred to by the cultivar name 'Balgalsabe'.

The new Geranium is a product of a planned breeding program conducted by the Inventor in Arroyo Grande, Calif. The objective of the breeding program was to develop new cultivars with the combination of the spreading growth habit of Ivy Geraniums with the large spherical umbels of Zonal Geraniums; freely-branching growth habit; medium green-colored leaves; and attractive flower and foliage colors.

The new Geranium originated from a self-pollination of the interspecific *Pelargonium×hortorum×P. peltatum* cultivar 'Sunrise', disclosed in U.S. Plant Pat. No. 10,139. The cultivar 'Balgalsabe' was discovered and selected by the Inventor as a flowering plant within the progeny of the stated cross in a controlled environment in Arroyo Grande in 1997.

Asexual reproduction of the new cultivar by terminal cuttings taken at Arroyo Grande has shown that the unique features of this new Geranium are stable and reproduced true to type in successive generations of asexual reproduction.

SUMMARY OF THE INVENTION

The following traits have been repeatedly observed and are determined to be the unique characteristics of 'Balgalsabe'. These characteristics in combination distinguish 'Balgalsabe' as a new and distinct cultivar:

1. Semi-double dark red-colored flowers.
2. Very freely flowering.
3. Upright and rounded to spreading growth habit.
4. Freely basal-branching habit.

The new Geranium can be compared to the parent cultivar, 'Sunrise'. However, in side-by-side comparisons conducted in Arroyo Grande, plants of the new Geranium differ from plants of the cultivar 'Sunrise' in the following characteristics:

1. Plants of the new Geranium are smaller and not as vigorous as plants of the cultivar 'Sunrise'.
2. Plants of the new Geranium are more freely branching than plants of the cultivar 'Sunrise'.
3. Plants of the new Geranium have leaves with a sharply crenate margin whereas plants of the cultivar 'Sunrise' have leaves with a less sharply crenate margin.
4. Plants of the new Geranium have semi-double flowers whereas plants of the cultivar 'Sunrise' have single flowers.
5. Plants of the new Geranium have shorter peduncles than plants of the cultivar 'Sunrise'.

BRIEF DESCRIPTION OF THE PHOTOGRAPH

The accompanying photograph illustrates the overall appearance of the new cultivar as true as it is reasonably possible to obtain in colored reproductions of this type. Colors in the photographs may differ slightly from the color values cited in the detailed botanical description which accurately describe the actual colors of the new Geranium. The photograph comprises a top perspective view of a typical flowering plant of 'Balgalsabe'.

DETAILED BOTANICAL DESCRIPTION

The cultivar 'Balgalsabe' has not been observed under all possible environmental conditions. The phenotype may vary somewhat with variations in environment such as temperature and light intensity, without, however, any variance in genotype. The following observations and measurements describe plants about 10 weeks after planting rooted cuttings and grown in 10-cm pots in West Chicago, Ill., under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Pelargonium×hortorum×P. peltatum* cultivar 'Balgalsabe'.

Parentage: Self pollination of *Pelargonium×hortorum×P. peltatum* cultivar 'Sunrise', disclosed in U.S. Plant Pat. No. 10,139.

Propagation:

*Type cutting.*—Terminal cuttings.

*Time to initiate roots.*—About 7 days at temperatures about 18° C.

*Time to develop roots.*—About 21 days at temperatures about 18° C.

*Root description.*—Fibrous and freely branching.

Plant description:

*General appearance.*—Upright and rounded to spreading growth habit. Appropriate for 10 and 12.5-cm containers.

*Crop time.*—Starting with a rooted cutting, about ten weeks are required to produced a finished flowering plant in 10-cm container.

*Growth and branching habit.*—Moderately vigorous and freely basal-branching with about six lateral branches.

*Plant height* (*to top of foliage*).—About 26.3 cm.

*Plant width.*—About 28 cm.

*Lateral branches.*—Length: About 22 cm. Internode length: About 3.4 cm. Color: 144A.

*Foliage description.*—Leaves simple, generally symmetrical, abundant, opposite. Length: About 5.3 cm. Width: About 8.6 cm. Shape: Reniform. Apex: Rounded. Base: Cordate. Margin: Lobed, sharply crenate. Venation: Palmate. Texture: Both surfaces pubescent; rough. Color: Fully expanded foliage, upper surface: 137A. Fully expanded foliage, lower surface: 137C. Venation, both surfaces: 144B. Zonation: Close to 147A. Petiole: Length: About 5 cm. Diameter: About 2 mm. Color: Close to 144A.

Flower description:

*Flower type and habit.*—Flowers arranged in spherical umbels arising from apical leaf axils. Umbels displayed above or beyond the foliage. At full flowering, usually about six open umbels and about four developing umbels per plant. Flowers semi-double and rounded. Freely and continuously flowering: persistent. Not fragrant.

*Flowering season.*—Year-round under greenhouse conditions. In the garden, flowering is continuous from spring until fall.

*Umbels.*—Number of flowers per umbel: About 17. Diameter: About 7.3 cm. Height: About 5.5 cm.

*Flowers.*—Diameter: About 4.5 cm. Depth (height): About 1.7 cm.

*Flower buds.*—Length: About 1.2 cm. Diameter: About 7 mm. Shape: Elliptic. Color: Close to 44B.

*Petals/petaloids.*—Quantity: About five petals and about eight petaloids per flower. Arrangement: Upper petals, imbricate; lower petals, imbricate; upper petals do not overlap lower petals; petaloids, not overlapping. Petal length: About 2.4 cm. Petal width: About 1.8 cm. Shape: Petals, narrow obovate; petaloids, irregular. Petal apex: Rounded. Petal base: Attenuate, pointed. Petal margin: Entire. Petal texture: Smooth. Color, fully opened flowers: Petals and petaloids, upper surface: Between 44A and 45B; venation, 53B towards base. Petals and petaloids, lower surface: 44B; venation, 45B.

*Sepals.*—Quantity: About five; not overlapping. Length: About 1 cm. Diameter: About 3 mm. Shape: Linear. Apex: Acuminate. Margin: Entire. Texture: Pubescent. Color: Both surfaces, 185A; apex, 146C.

*Peduncle* (*unbel stem*).—Length: About 17.8 cm. Angle: Erect. Strength: Moderately strong. Texture: Pubescent; short and stiff hairs. Color: Close to 144A.

*Pedicel* (*individual flower stem*).—Length: About 2.4 cm. Angle: Erect. Strength: Moderately strong. Texture: Many short soft hairs. Color: Between 185A and 187B.

*Reproductive organs.*—Androecium: Anther size: About 3 mm. Pollen: Moderate. Pollen color: 28A. Gynoecium: Pistil number: One. Pistil length: About 1.1 cm.

Disease resistance: Plants of the new Geranium have not been observed to be resistant to pathogens common to Pelargonium.

Seed development: Seed production has not been observed.

It is claimed:

1. A new and distinct cultivar of Geranium plant named 'Balgalsabe', as illustrated and described.

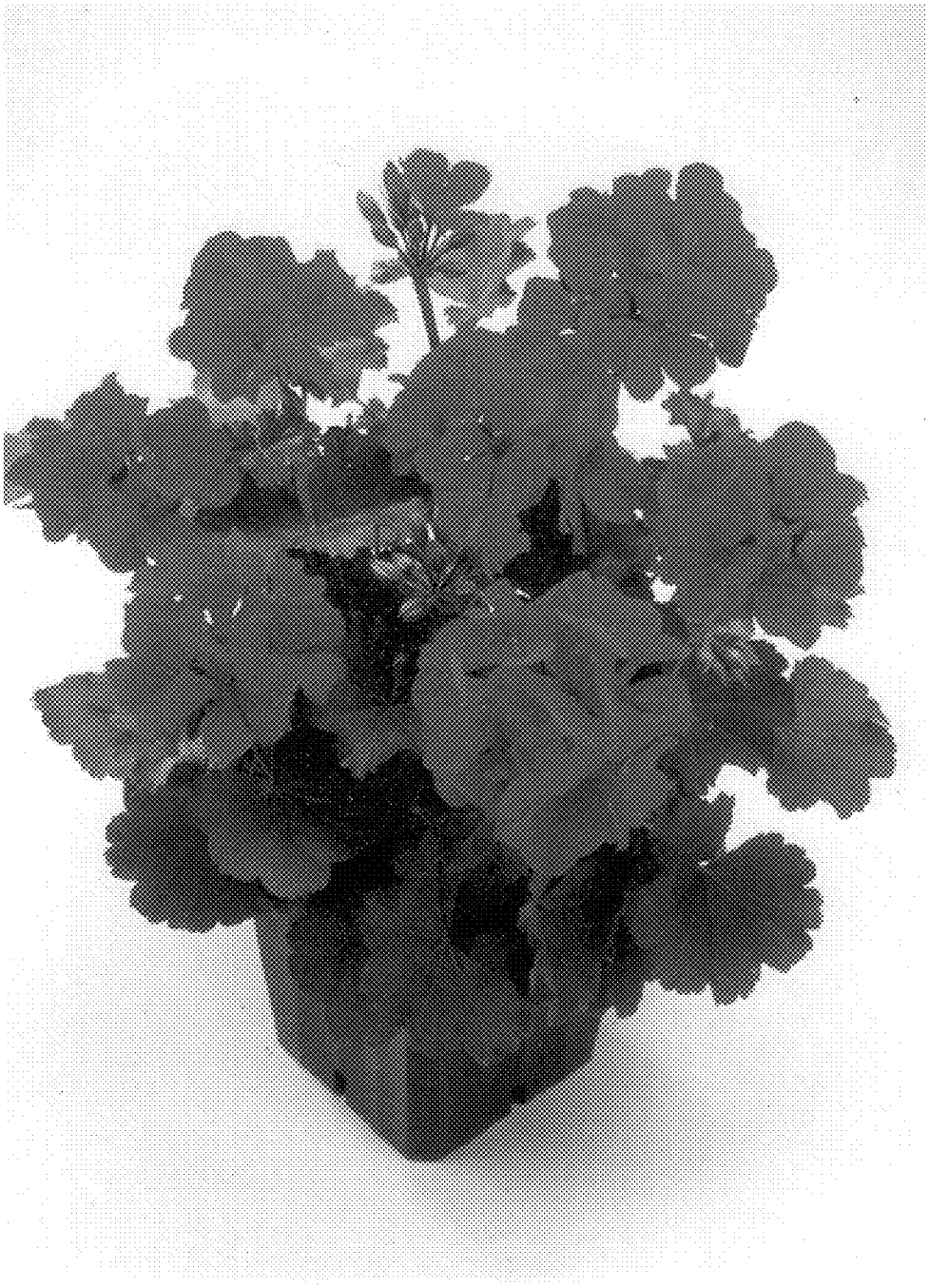

* * * * *